United States Patent [19]

Rhodes et al.

[11] Patent Number: 4,605,752

[45] Date of Patent: Aug. 12, 1986

[54] QUATERNARY AMMONIUM TETRATHIOVANADATES

[75] Inventors: Richard P. Rhodes, Westfield; Thomas R. Halbert, Annandale, both of N.J.

[73] Assignee: Exxon Research and Engineering Co., Florham Park, N.J.

[21] Appl. No.: 669,900

[22] Filed: Nov. 9, 1984

[51] Int. Cl.$^4$ .............................................. C07F 9/00
[52] U.S. Cl. ............................................................ 556/42
[58] Field of Search .................................... 260/429 R

[56] References Cited

U.S. PATENT DOCUMENTS

| | | | |
|---|---|---|---|
| 3,254,102 | 5/1966 | Swanson | 260/429 R |
| 3,294,828 | 12/1966 | Werner | 260/429 R |
| 3,297,733 | 1/1967 | Kornicker | 260/429 R |
| 3,346,604 | 10/1967 | Roberts, Jr. | 260/429 R |
| 3,418,303 | 12/1968 | Barney et al. | 260/429 R X |
| 3,632,658 | 1/1972 | Halasa et al. | 260/665 |
| 4,094,893 | 6/1978 | Dines | 260/429 R |
| 4,309,310 | 1/1982 | Callahan | 260/429 R X |
| 4,343,746 | 8/1982 | Anglin et al. | 260/429 R |
| 4,343,747 | 8/1982 | Ryu et al. | 260/429 R |

FOREIGN PATENT DOCUMENTS 1577293  8/1969  France .

Primary Examiner—Helen M. S. Sneed
Attorney, Agent, or Firm—E. Thomas Wheelock

[57] ABSTRACT

This invention relates to a composition of matter comprising an ammonium tetrathiovanadate having the following formula:

$$(R_1R_2R_3R_4N)_3VS_4$$

wherein $R_1$, $R_2$, $R_3$, $R_4$ may each be independently an alkyl group having from 1 to 30 carbon atoms or an aryl or alkylaryl group having from 6 to 30 carbon atoms. The preferred composition comprises (trioctylmethylammonium)$_3$VS$_4$.

9 Claims, 1 Drawing Figure

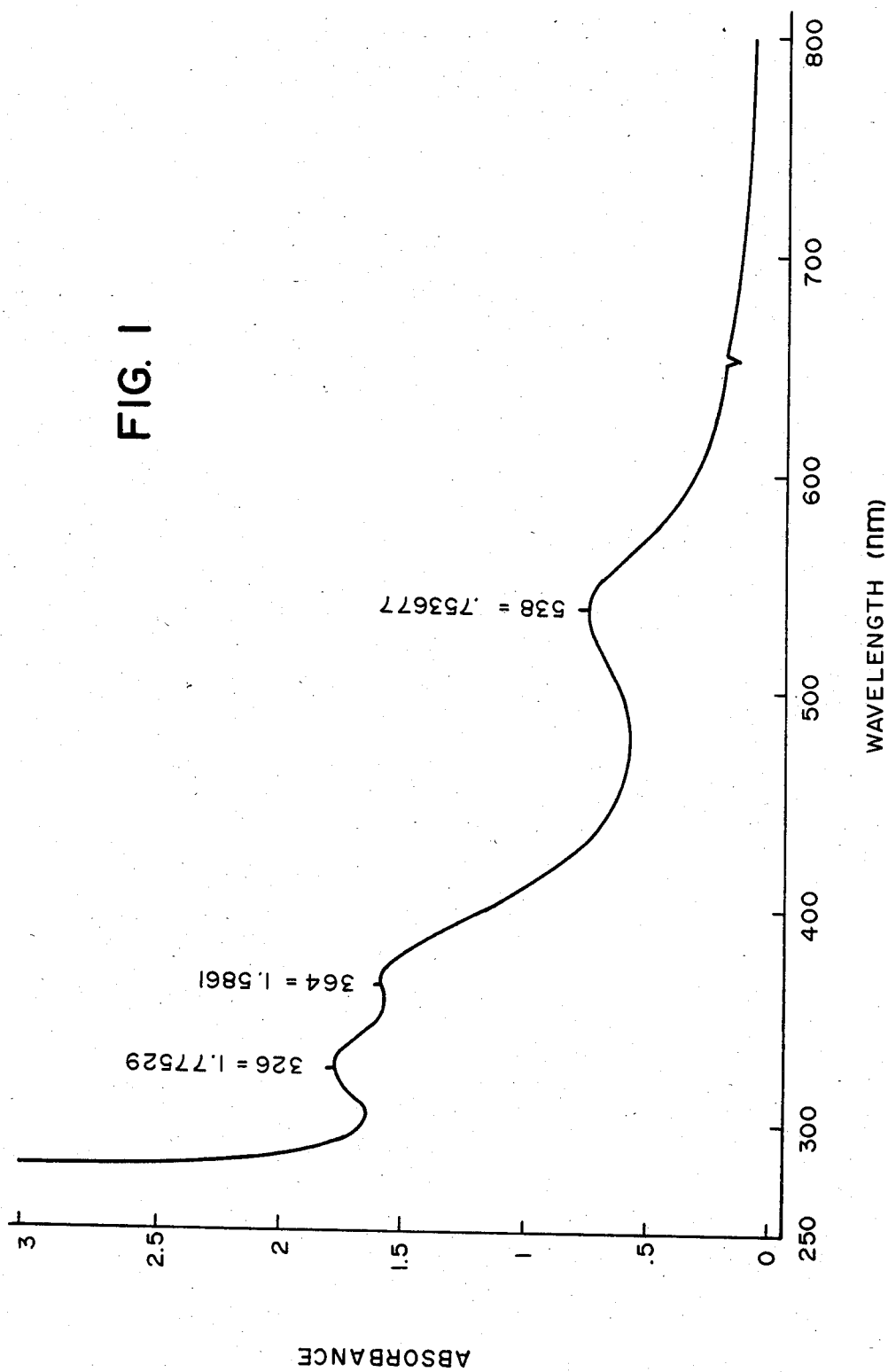

QUATERNARY AMMONIUM TETRATHIOVANADATES

FIELD OF THE INVENTION

This invention relates to a composition of matter $(R_1R_2R_3R_4N)_3VS_4$ and a method of making that composition; where $R_1$, $R_2$, $R_3$, $R_4$ may each be, independently, an alkyl group having from 1 to 30 carbon atoms or an aryl or alkylaryl group having from 6 to 30 carbon atoms. The preferred composition is (trioctylmethyl ammonium)$_3$VS$_4$.

BACKGROUND OF THE INVENTION

Other documents disclosing the existence of vanadium- and nitrogen-containing organic compounds are known.

For instance, U.S. Pat. No. 3,632,658 to Halasa, issued Jan. 4, 1972, discloses an organo-ammonium vanadium oxide which is the reaction product of $NH_4VO_3$ and a quaternary ammonium chloride.

Similarly, French Pat. No. 1,577,293 discloses various organo-vanadium compounds which are prepared by reacting a compound of formula I or II with a compound of formula III $$R_1R_2R_3R_4{}^+X^-  \quad [I]$$

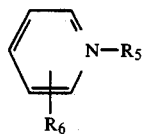
[II]

$$aM_2O \cdot bV_2O_5 \cdot nH_2O  \quad [III]$$

where $R_1$ is $C_{6-21}$ hydrocarbyl or a derivative; $R_{2-4}$ are each H or a hydrocarbyl; X is an anion; $R_5$ is $C_{1-12}$ alkyl, phenyl, benzyl —COOR$_6$ or —CH$_2$NHCOR$_6$; $R_6$ is $C_{1-12}$ alkyl or halogen; M is NH$_4$ or a metal cation; "a" and "b" are integers; and "n" is 0–18.

U.S. Pat. No. 4,094,893 to Dines, issued June 13, 1978, discloses isonitrile intercalation complexes having the formula:

$$TX_2(RNC)_y$$

wherein $TX_2$ is the inorganic host in which T is selected from titanium, zirconium, hafnium, vanadium, niobium, tantalum, molybdenum, tungsten and mixtures thereof; and X is selected from sulfur, selenium or tellurium. The group RNC is the organic guest wherein R is an alkyl or arylalkyl radical of from 1 to 18 carbon atoms "y" is a number ranging from about 0.10 to about 2.0.

None of these documents suggests a reaction which produces an organic ammonium tetrathiovanadate.

BRIEF DESCRIPTION OF THE DRAWINGS

FIG. 1 is visible light spectrum absorbance graph of (trioctyl-methyl-ammonium)$_3$VS$_4$ in toluene.

DESCRIPTION OF THE INVENTION

As mentioned above, this invention relates to a composition of matter having the formula:

$$(R_1R_2R_3R_4N)_3VS_4$$

wherein $R_1$, $R_2$, $R_3$, and $R_4$ may each be, independently, an alkyl group having from 1 to 30 carbon atoms or an aryl or alkylaryl group having from 6 to 30 carbon atoms. The total number of carbon atoms $R_1$, $R_2$, $R_3$, $R_4$ is no less than 12. The most preferred composition is wherein $R_1$ is a methyl group and $R_2$, $R_3$, and $R_4$ are alkyl groups having 8 carbon atoms.

The invention also includes a non-limiting method for making the noted composition.

The process involves reacting a compound having the following formula:

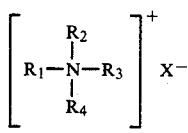

wherein $R_1$, $R_2$, $R_3$, $R_4$ are independently an alkyl group having from 1 to 30 carbon atoms or an aryl or alkyl-aryl group having from 6 to 30 carbon atoms and X is an anion, preferably one which forms a solid reaction product with the other reactant. The most preferable anion X is chlorine although other anions including the other halogens, nitrate, sulfite, sulfate, etc. are acceptable. Preferably $R_1$ is a methyl group and $R_2$, $R_3$ and $R_4$ are $C_8$ alkyl groups. The choice of $R_1$, $R_2$, $R_3$ and $R_4$ depend upon the intended end use of the synthesized compound, e.g., the level of desired oil solubility, etc.

The other reactant is an ionic tetrathiovandate, preferably one which forms a solid or readily separable reaction product with the anion of the ammonium reactant. The most preferred reactant is (NH$_4$)$_3$VS$_4$.

The reaction conditions are not extreme in that the reaction takes place in the liquid phase at ordinary temperatures, e.g., $-20°$ to $150°$ C., and at autogeneous pressures. The reaction medium should generally be anhydrous and, if a gas phase is present, under an inert gas blanket such as nitrogen or helium. The medium may be a solvent, preferably an organic solvent of moderate to low polarity, such as toluene, and containing a small amount of a nonreactive polar material such as dimethyl formamide or trioctyl phosphine oxide. The nonreactive polar material acts as catalyst or, at least, as a cosolvent.

The reaction itself proceeds to equilibrium with substantially stoichiometric proportions of the reactants. A slight excess of the thiovanadate reactant is desirable but not necessary. The unreacted excess may be removed by filtration.

Once the reaction is complete, the extraneous reaction product, desirably ammonium chloride, and excess thiovanadate, may be separated from the reaction medium by filtration. The solvent and catalyst may be evaporated leaving the desired quaternary ammonium thiovanadate product. The product, on the other hand, may be often used in toluene solution.

Although these compositions have utility as homogeneous catalysts; they have special utility in the preparation of hydroconversion catalysts.

A non-limiting example showing the operation of the inventive process and the most preferred product is as follows.

EXAMPLE

A dry solution of 2% dimethyl formamide in toluene was placed in a stirred reactor. The reactor was maintained at 25° C. under an atmosphere of dry $N_2$. An amount of a dry (trioctyl-methyl)$_3$Cl, sold commercially as Aliquat ® chloride by the Henkel Corp., was added to the reactor. Ammonium thiovanadate was added in a nearly stoichiometric amount, i.e., a slight excess of thiovanadate, according to the following equation:

3(trioctyl-methyl-ammonium)Cl + $(NH_4)_3VS_4$ 

3$NH_4Cl$ + (triocytyl-methyl-ammonium)$_3VS_4$.

The reaction mixture was stirred for 12 hours. The crystalline ammonium chloride and a trace of unreacted ammonium thiovanadate were filtered off and both the solvent and catalyst (or cosolvent) were removed by evaporation. The product (trioctyl-methyl-ammonium)$_3VS_4$ was a purple oil having the visible absorbance spectrum in toluene shown in FIG. 1.

Having thus described the invention, it should be apparent that variations in amounts and reactants and conditions of operation would be readily apparent to one having ordinary skill in this art and those variations would be within the spirit of the invention as set forth in the appended claims.

We claim as our invention:

1. A quaternary ammonium tetrathiovanadate having the following formula:

$(R_1R_2R_3R_4N)_3VS_4$ wherein $R_1$, $R_2$, $R_3$, $R_4$ may each be independently an alkyl group having from 1 to 30 carbon atoms or an aryl or alkylaryl group having from 6 to 30 carbon atoms.

2. The tetrathiovanadate of claim 1 wherein the total number of carbons in $R_1$, $R_2$, $R_3$ and $R_4$ is no less than 12.

3. A composition comprising (trioctylmethyl-ammonium)$_3VS_4$.

4. A method for producing a quaternary ammonium tetrathiovanadate having the following formula:

$(R_1R_2R_3R_4N)_3VS_4$ wherein $R_1$, $R_2$, $R_3$, $R_4$ may each be independently an alkyl group having from 1 to 30 carbon atoms or an aryl or alklyaryl group having from 6 to 30 carbon atoms comprising the steps of:

placing in a substantially nonpolar and nonreactive solvent containing an effective catalyst under reaction conditions an ammonium reactant having the formula $R_1R_2R_3R_4NX$, wherein X is an anion, and ammonium thiovanadate, and recovering the quaternary ammonium tetrathiovanadate.

5. The process of claim 4 wherein the anion X is chlorine.

6. The process of claim 5 wherein $R_1$ is a methyl group, and $R_2$, $R_3$, and $R_4$ are $C_8$ alkyl groups.

7. The process of claim 4 wherein the nonpolar and nonreactive solvent is toluene.

8. The process of claim 4 wherein the effective catalyst is a nonreactive polar material.

9. The process of claim 7 wherein the effective catalyst is selected from dimethyl formamide and trioctylphosphine oxide.

* * * * *